(12) United States Patent  
Carr

(10) Patent No.: US 7,751,053 B2  
(45) Date of Patent: Jul. 6, 2010

(54) OPTICAL DETECTION AND ANALYSIS OF PARTICLES

(76) Inventor: Robert Jeffrey Geddes Carr, Wayside, Thorneydown Road, Winterbourne Gunner, Salisbury (GB) SP4 6LN ( * ) Notice: Subject to any disclaimer, the term of this patent is extended or adjusted under 35 U.S.C. 154(b) by 74 days.

(21) Appl. No.: 12/144,770

(22) Filed: Jun. 24, 2008

(65) Prior Publication Data

US 2008/0252884 A1    Oct. 16, 2008

Related U.S. Application Data

(63) Continuation of application No. 10/513,160, filed as application No. PCT/GB03/01827 on Apr. 29, 2003, now Pat. No. 7,399,600.

(30) Foreign Application Priority Data

Apr. 29, 2003   (GB) ................................. 0209666.7

(51) Int. Cl.  
   *G01N 21/55* (2006.01)
(52) U.S. Cl. ..................................................... 356/445
(58) Field of Classification Search ................. 356/445, 356/446, 317–318, 335, 450, 448; 435/6, 435/7.1, 7.2; 422/52, 82.05, 164, 172, 68.1; 436/172, 524, 526, 536–537; 204/400, 403, 204/298.16  
See application file for complete search history.

(56) References Cited

U.S. PATENT DOCUMENTS

2002/0094528 A1 *   7/2002   Salafsky ........................ 435/6  
2004/0046962 A1 *   3/2004   Luber .......................... 356/445

* cited by examiner

*Primary Examiner*—Tarifur Chowdhury  
*Assistant Examiner*—Michael LaPage  
(74) *Attorney, Agent, or Firm*—Barnes & Thornburg LLP

(57) ABSTRACT

Method and apparatus for the single particle detection of submicron structures such as biological molecules and viruses utilises an optical element (100) comprising an optically transparent substrate (1) partially coated with a thin film of metal (2) illuminated with an optical beam (4) incident on a non-metal coated region (3) of the surface of the optical element at a point adjacent or close to the metal coated region of the optical element such that the beam propagates above but close and substantially parallel to the metal surface defining a measurement zone from within which submicron particles (7) contained in a sample (6) placed in contact with the optical element scatter or emit light which can be detected in the far field by conventional photodetection systems. The apparatus can be configured in a flow cell or optical microscope configuration.

9 Claims, 2 Drawing Sheets

OPTICAL DETECTION AND ANALYSIS OF PARTICLES

This application is a continuation of U.S. patent application Ser. No. 10/1513,160, filed Oct. 29, 2004, now U.S. Pat. No.7,399,600, which is the national filing of International Application No. PCT/GB03/01827, filed Apr. 29, 2003, claiming priority to British Application No. 0209666.7 filed Apr. 29, 2002.

The present invention relates to the optical detection and analysis of particulates of nanometer, sub-micron or micron dimensions.

A large number of principles and techniques exist by which particles can be analysed in terms of their number, size, shape, composition and motion. Historically, the observation and characterisation of particles lies in the domain of microscopy in which highly magnified images of particles are generated through the use of high powered lensed systems and which can be seen directly by eye or can be captured by camera for subsequent interpretation by the operator or by an image analysis system.

There are many types of microscope systems capable of characterising the particle in terms of its interaction with the incident illumination. For instance, the particle may selectively absorb certain wavelengths of the light such as in differential absorption, the technique most common in conventional transmission microscopy. Other microscopical variants exist which selectively monitor specific wavelengths generated by the particle when illuminated by the incident illumination, such as fluorescent microscopy which is useful in reducing background interference and which can be used to identify specific structures through the use of fluorescent labels. Yet other microscopical techniques utilise the way in which the particle induces a phase shift in the incident light, such as phase contrast or interference microscopy. Other microscope techniques, such as epiluminescent microscopy, employ light scattering at high angles to allow low contrast particles to be visualised against non-illuminated background. Other similar versions of this technique are used in microscopy, of which the most common is referred to as dark field microscopy. In this case, the sample is illuminated by a high numerical aperture source and the central portion of the illuminating cone is blocked from entering the detection objective by an optical stop so that the particle is illuminated at an oblique angle only.

Methods of illumination vary greatly and in certain circumstances the sample (typically an aqueous suspension of particles) can be placed on a transparent (typically glass or silica) optical substrate which is illuminated by a suitably defined and collimated optical beam at a certain angle called the critical angle at which the incident light is refracted along the plane of the optical element on which the liquid sample is placed. A small portion of the beam, called the evanescent wave, propagates a small distance into the sample phase above the optical substrate and particles entering this evanescent region act to scatter some of this otherwise non-radiative field. The light coupled out (i.e. scattered by the particle within the evanescent field) can then be detected in the far field either by eye or by a suitable detector situated normal or at high angle to the plane of the surface. When employed in a microscope configuration this technique is referred to as evanescent field microscopy and relies on the principle of frustrated total internal reflection Numerous non-imaging methods exist for the optical analysis of suspensions μm or sub-μm particles or solutions of nm scale particles such as biological molecules or macromolecules. Many such techniques monitor the interaction between biological molecules and in order to define a region within such interactions can be specifically detected within minimal interference from other species in the bulk of the solution phase, such analyses are frequently carried out at the interface of an optical waveguide or fibre optic structure onto the surface of which have been immobilised biological capture molecules such as antibodies, specific for the target analyte. In conventional waveguide or fibre optic systems use is made of the changes in the refractive index properties at the surface interface following binding of specific biological molecules in the surface associated evanescent field region of the optical structure. This field extends, however, only some 100-200 nm into the bulk solution phase and is accordingly limited in its ability to monitor weak interactions involving limited numbers of molecular interactions. Such a method is disclosed in DE 4307042 (930305), in which a single or multilayer of receptor molecules are deposited on an evanescent waveguide sensor device and which is capable of sensing and quantifying various chemical and biochemical species in solution. A similar method is disclosed in WO 9005295 claiming priority of SE 884075 (881110) in which a wedge shaped prism is used to allow light reflected at different angles off the underside of the optical sensor element to be imaged and analysed to quantify specific species in solution. Similarly, EP677735 claiming priority of U.S. Pat. Nos. 228,233 (940,415) describes an optical resonator cavity in which light is reflected from a total internal reflector (TIR) cavity in contact with a solution components of which interact with the evanescent field within the TIR cavity allowing quantification of species in the solution. These techniques are characterised by their reliance on the analysis of light which is reflected from the underside of a sensing element surface.

The ability to follow such low numbers of interactions or binding events can, however, be significantly enhanced, by one or two orders of magnitude, by employing Surface Plasmon Resonance techniques in which the surface of the optical waveguide structure is coated with a thin film of a conductive metal, typically gold, silver or aluminium, in which electromagnetic waves, called Surface Plasmons, can be induced by a beam of light incident on the metal-glass interface at a specific angle called the Surface Plasmon Resonance angle. Modulation of the refractive index of the interfacial region between the solution and the metal surface following binding of the captured macromolecules causes a change in the SPR angle which can either be measured directly or which causes the amount of light reflected from the underside of the metal surface to change. Such changes can be directly related to the mass and other optical properties of the molecules binding to the SPR device surface. Several biosensor systems based on such principles have been disclosed. Thus WO 9005305 claiming priority of SE884074 (881110) describes the use of a metal film deposited on one side of a block unit of optical instrumentation, one multi-functionalised side of which is in contact with a solution of reagents or samples to be measured, the other side is illuminated by an optical beam within the block unit of optical instrumentation caused to reflect off the metal surface at an angle such that reflectance is modified by selective binding of ligands on the functionalised surface. Measurement of the reflected beam can be correlated to concentrations of specific species binding to the functionalised sensor surface.

Similarly EP 341927 claiming priority of GB881154 (880510) describes a biological or biochemical testing sensor comprising a surface plasmon resonance (SPR) sensor and a sample-antibody surface arranged to influence resonance characteristics. The SPR sensor comprises a metallised glass slide onto the glass-metal interface of which is directed a beam of light at an angle at which surface plasmons are induced to resonate in the metal film. Changes in the resonance angle on binding of analyte are determined by measuring the intensity or angle of the light internally reflected from the metal-glass interface. Such non-imaging reflectance techniques monitor only the binding of relatively large numbers of macromolecules through measurement of changes in the amount or position of the reflected light As with the evanescent techniques described above, these techniques are characterised by their reliance on measuring the intensity of light reflected from the surface or changes in the resonance angle on binding of specific sample components.

A modification of such SPR devices has been described which can be used to locate, visualise, detect or count the presence of individual macromolecules or very sub-µm particulates in which the optical effect of interaction of individual m or very sub-µm scale structures with the evanescent surface plasmon resonance field causes light to be scattered from such structures into the far field at high angles. Thus WO 98/57148 and U.S. Ser. No. 09/308,049 claiming priority of PCT/GB98/01591 describes a method and apparatus for the single particle detection of submicron structures such as biological molecules and viruses which utilises an optically transparent substrate coated with a thin film of metal which is illuminated with an optical beam incident at surface plasmon resonance angle wherein submicron particles contained in a sample placed in contact with the metal film scatter light which can be detected in the far field by conventional photo-detection systems. The apparatus can be configured in a flow cytometric or optical microscope configuration.

Similarly, WO 98/22808 and WO0142768 describe a surface plasmon resonance apparatus for detecting a soluble analyte (e.g. a protein) or a particulate analyte (e.g. a cell), the apparatus comprising a sensor block adapted to receive a sensor, said sensor, for example a sensor slide, having a metallized sensor surface capable of binding the analyte; a light source capable of generating an evanescent surface plasmon resonance wave at the sensor surface of a sensor slide on the sensor block; a first detector capable of detecting light from the light source which is internally reflected from the, sensor surface; and a second detector (e.g. a video camera) capable of detecting light scattered or emitted from an analyte bound thereto. Optionally the apparatus further comprises a second light source for increasing the intensity of the light scattered or emitted from an analyte bound to the sensor surface, preferably, this is sited to such as to minimize the amount of light transmitted therefrom which is detected by the first detector. Also disclosed are sensors adapted for use in the apparatus, and methods of detecting analytes in samples comprising exposing samples to the sensor surface of the apparatus.

In both the above cases employing the surface plasmon resonance phenomenon, it is necessary for the illuminating beam to be incident on the underside of the metal film in contact with the underlying optically transparent substrate in order to induce surface plasmons at the metal surface, energy from the evanescent field associated with which is then scattered into the far field by the target particulates within the evanescent field. Furthermore, the angle at which the incident illumination must strike the underside of the metal film in order to excite surface plasmons in the metal film surface is very narrow and requires careful alignment of the component optical elements. Finally, the amount of energy coupled through the metal from the incident illuminating beam to the evanescent surface plasmon field is frequently insufficient for the particles interacting with said field to scatter sufficient energy to the detectors to allow very small, for example less than 200 nm, particles to be visualised. Thus WO0142768 is limited to describing the visualisation of bacterial cells by this technique by way of example, such particles being in excess of 500 nm in diameter.

If generation of images of individual particles is not required, for instance when it is necessary only to determine the presence or otherwise of particles and/or to estimate their size, size distribution, number etc., then other principles in which light scattering phenomena predominate may be used. Such methods rely on the measurement of the amplitude of optical signal generated by the interaction of particles with suitably intense and focused beams of light (typically from laser sources), each particle passing through the optical measurement zone in which the interrogating beam is caused to pass, signals generated by the interaction of the particle with the optical beam being detected by suitable photosensitive devices such as photomultiplier tubes, photodiodes, CCDs and the like.

Such instruments are referred to as particle detectors or particle counters and are used widely in a variety of industrial and scientific applications. One such technique, known as flow cytometry, allows particles in a concentrated suspension, to be addressed on an individual basis by diluting the sample through adding it slowly to a rapidly flowing hydrodynamic sheath of substantially particle free liquid, the output of which is directed by a finely adjusted nozzle to flow accurately through a finely focused interrogating laser beam which constitutes a measurement volume. By measuring the intensity of scattered light and where applicable, the fluorescence wavelength generated by the interaction of the particle with a suitably focused and intense optical source, particles as small as 0.2 µm can be quantified and various optical parameters relating to their size and differential absorption or fluorescence characteristics can be determined.

Below a certain particle size limit, however, the signal generated by the interaction of the particle with the interrogating beam of light is insufficient for it to be distinguished from the background inherent in such optical light scattering instrument configurations. Increasing the intensity of the interrogating optical beam acts merely to increase the intensity of background as well as the signal generated by the particle. To determine the presence of such very sub-micron particles it is normally usual to employ higher resolution non-optical techniques such as electron microscopy but these suffer from significantly higher complexity and cost.

There is therefore a need for a simple, robust and low cost optical particle detection system capable of detecting the presence of very small particles (such as those, for example, substantially below ¼ of the wavelength of illuminating radiation) on an individual basis without the need for expensive, high powered and hazardous optical sources, which does not rely on the phenomenon of scattering of the evanescent field associated with resonant surface plasmons. Preferably such apparatus should be compatible with existing optical microscopes and particle detection apparatus, simple to use and operate and capable of furnishing information, such as particle size, size distribution, number and other optical parameters on suspensions of particles of mixed characteristics in a frequently complex background.

For the avoidance of doubt, the content of all publications mentioned in this specification is incorporated herein by reference.

SUMMARY OF THE INVENTION

The present invention is based at least in part on the unexpected finding that when a small volume of a suspension of sub-micron particulates, exemplified by virus particles, is placed onto the surface of an optical element comprising, for example, an optically transparent (typically glass or silica) substrate, one part of the surface of which has been coated with a thin (e.g. 10's nm) film of metal, for example chrome, silver or gold which is at least partially optically opaque, such that a further adjacent region of the optically transparent substrate is left uncoated by the metal film and which non-metal coated region is illuminated by a beam of light caused to be incident on it, or in close proximity to it, at a point which is close (e.g. within 5 mm, preferably within 1 mm, more preferably within 0.5 mm) to (but typically not coincident with) the metal film coated region and at an angle such that the optical beam is caused to propagate, by refraction, through the sample substantially parallel to, and at a small distance above, the adjacent metal film, individual sub-micron particles within the path of the beam passing through the sample above the metal film are found to scatter sufficient amounts of light so as to be individually discernible through a conventional microscope objective/lens combination, by eye or by a suitable photodetector such as a photon multiplier tube, solid state photodiode, CCD camera or other photosensitive device placed in an image plane in the far field and normal or at high angle to the plane of the otherwise non-radiative metallised surface. The particles capable of being thus individually detected are of a dimension such that they would not otherwise have been detectable by conventional optical transmission, dark-field, phase contrast, evanescent field or surface plasmon resonance microscopical techniques such as those described above.

The sample will typically, but not necessarily, comprise a liquid comprising a suspension or other dispersion of particles. The particles may be solid or may conceivably be liquid (e.g. fine droplets in an emulsion). A liquid sample will normally, but not inevitably, be an aqueous liquid.

In general terms, the present invention provides apparatus for the detection and/or analysis of individual sub-micron particles in a sample, the apparatus comprising: a substrate, means for illuminating the substrate with a focused optical beam, and means for individually detecting the optical radiation from individual particles in a sample placed on the coated portion of the substrate surface through their interaction with the optical beam.

Components generally suitable for use in the apparatus of the invention are disclosed in, inter alia, U.S. Pat. No. 6,280,960.

The person skilled in the art will understand that, whilst preferably the substrate per se is wholly or substantially transparent to the beam of electromagnetic radiation, the opaque coating is sufficient to render substantially or wholly opaque that portion of the substrate the surface of which is so coated.

Typically the beam of electromagnetic radiation is caused to be incident upon the substrate surface opposed to that which is partially coated with the opaque coating, the beam then being propagated along the desired path, through the sample, by refraction through the substrate, it therefore being a requirement in such an embodiment that the substrate is wholly or substantially transparent to the electromagnetic radiation, and that at least a portion of the surface of the substrate is not covered with the opaque coating.

It is at least conceivable however that in other embodiments the beam of electromagnetic radiation may be directly incident upon the sample without having first passed through the substrate e.g. by passing the beam in close proximity to the substrate directly parallel to the coated surface of the substrate or at a slight "grazing" angle thereto, or in another embodiment that the electromagnetic radiation is caused to pass through the sample by reflection from the upper surface of the substrate (i.e. that the beam is incident upon the same side of the substrate as that which is at least partially coated with the opaque coating). In these embodiments there is no requirement that the substrate be wholly or partially transparent and no requirement that at least a portion of the substrate surface is left uncoated.

The electromagnetic radiation will typically have a wavelength in the range $1 \times 10^{-8}$ to $1 \times 10^{-5}$ nm (i.e. in the range from far ultra-violet to deep infra-red). Conveniently the electromagnetic radiation will be light of a wavelength visible to the human eye (i.e. in the range from about 3 to $8 \times 10^{-7}$ nm). The electromagnetic radiation will conveniently be a focused beam of visible light, and the apparatus will advantageously comprise suitable lens or other focusing means. A suitable electromagnetic radiation source is a laser.

Typically the substrate will comprise glass or silica and be optically transparent at wavelengths visible to the human eye.

In some embodiments it is preferred if the opaque coating is reflective. The inventor has so far found an opaque metallic coating to be particularly suitable. The thickness of the opaque coating is preferably less than 500 nm, more preferably less than 250 nm, and most preferably less than 100 nm.

The edge of the beam of electromagnetic radiation, defined by its $1/e^2$ point, is preferably caused to propagate less than 2 μm above the coated surface of the substrate, more preferably less than 1 μm and most preferably less than 500 nm. Further, the beam is preferably caused to be propagated substantially parallel to the coated surface of substrate i.e. at an angle to the plane of the surface of less than 5.degree., preferably less than 2.degree., more preferably less than 1.degree., and most preferably less than 0.5.degree., and the term "slight angle" should be construed accordingly for the purposes of the present specification.

The invention also provides a corresponding method.

In a preferred embodiment according to the present invention there is provided a method and apparatus for the individual optical detection and/or characterisation of small (relative to the wavelength of light being used for illumination) particles suspended in a transparent liquid or gas medium (e.g. for the purposes of determining particle characteristics such as size, size distribution, number concentration, shape or other optical characteristics such as fluorescence, polarisation, phase modulating properties, etc.) wherein a sample containing the suspended particles is placed onto the surface of an optical element comprising an optically transparent (e.g. glass or silica) substrate, one part of the surface of which has been coated with a thin (10's nm) film of metal, for example chrome, silver or gold which is at least partially optically opaque, such that a further adjacent region of the surface of the optically transparent substrate is left uncoated by the metal film and which non-metal coated surface region is illuminated by a beam of light caused to be incident on it at a point which is close to (but typically not coincident with) the adjacent metal film coating and at an angle such that the optical beam is caused to propagate, by refraction, through the sample substantially parallel with, or at a slight angle to, the plane of the metal film and at a small distance above the metal film, such that individual sub-micron particles within path of the optical beam passing through the sample above the metal film are found to scatter sufficient amounts of light so as to be individually discernible through a conventional microscope objective/lens combination, by eye or by a suitable photodetector such as a photon multiplier tube, solid state photodiode, CCD camera or other photosensitive device placed in an image plane in the far field and normal or at high angle to the plane of the coated surface. The particles capable of being thus individually detected are of a dimension such that they would not otherwise have been detectable by conventional optical transmission, dark-field, phase contrast, evanescent field or surface plasmon resonance microscopical techniques.

Advantageously, the presence of the opaque film below the path that is described by the optical beam acts to enhance the visibility of the particles resident therein, such particles, when below a certain dimension, scattering insufficient light to be visible when the metal film is absent. Accordingly the presence of an optically opaque (or substantially opaque) film on at least part of the surface of the substrate appears to be an essential feature of the invention.

Fluorescence emitted by, or light scattered from, the particles is seen, by eye or by suitable detectors, as a point of light arising from each particle in the measurement region, the amplitude of signal from each of which can be indicative of various optical properties of the particles as well as indicating its presence, size, motion, number, concentration, fluorescence, etc. all parameters of which can be quantified, if desirable, by suitable signal processing or image analysis instrumentation.

In accordance with the invention, microscope optics and instrumentation can be used to allow particles so small as to be otherwise undetectable by conventional optical microscopy techniques to be individually detected for the purposes of determination of particle presence, size, particle size distribution, concentration, number, fluorescent attributes (whether inherent or through the addition of fluorescent labels) for measurement of specific parameters associated with the particle composition, polarisation modifying properties, phase modulating properties or any other parameter normally addressable by optical methods of analysis.

In the particular case where the present method and associated apparatus could be used in conjunction with a non-microscopical application, such as in the case of a particle counting apparatus for the purposes of e.g. determining particle count as a function of size class, the particle suspension can be caused to flow over the surface of the optical element such that particulate suspensions that would otherwise be so dilute as to contain too few particles within the measurement volume for statistically accurate estimation of particle presence or number concentration or size distribution to be made, an increased volume of the particle-containing medium can be caused to flow over the detection region thereby increasing the number of particles capable of being accurately detected and analysed. For particle counting and analysis on such larger volumes the present method may be employed in an optical particle measurement and analysis system exemplified by those instruments known as flow cytometers in which a suspension of particles is caused to pass through an optical measurement region by introducing via a nozzle, the particulate-bearing sample into a stream of substantially particle free fluid moving at a higher velocity, known as a hydrodynamic sheath, such that the particle-bearing sample is diluted to the point where particles pass through the optical measurement region on an individual basis and the direction of the flow of particle-bearing sample can be finely adjusted to be optimally aligned with the optical measurement region. One type of flow cytometer employs what is known as a jet-on-an-open-surface (JOOS) configuration in which the sample bearing hydrodynamic sheath flow is played onto a flat, optically transparent surface such that the position of the sample stream can be finely adjusted through adjustment of the nozzle position and flow velocity to be more accurately placed at the waist of the interrogating optical beam. In accordance with the invention the use of a metallised optical surface, as described herein, advantageously allows smaller particles than would otherwise be optically detectable to be visualised in such a system by virtue of the enhancement of visibility afforded by the presence of the metal film as described above.

The process of the invention may thus be used to determine particle presence, size, particle size distribution, concentration, number, fluorescent attributes (whether inherent or through the addition of fluorescent labels) for measurement of specific parameters associated with the particle composition, polarisation modifying properties, phase modulating properties or any other parameter normally addressable by optical methods of analysis but which is particularly useful for carrying out such analyses on particles that are so small as to be otherwise undetectable on an individual basis by optical systems incorporating bulk lens configurations such as conventional microscopes, flow cytometers or other optical particle measurement instruments.

In this regard it has been found that the present invention allows sub-micron particles such as unlabelled viruses in solution or suspension to be directly visualised and counted on an individual basis through the use of optical sources of moderate power such as solid state laser devices of mW output.

The present invention, by virtue of its sensitivity to detection of particle-associated events close to a surface, further allows the interaction of sub-micron particles with surface coatings and functionalised layers to be individually monitored and analysed in time. Such events may include the interaction of discrete virus particles with a coating on the optical element specifically designed to substantially reproduce the properties exhibited by a cell surface for the purposes of investigating virus-cell envelope infection events.

Similarly, in accordance with the invention the adhesion of sub-micron regions of cell membranes or walls and regions thereof with surfaces, chemically or biochemically modified or otherwise, may be monitored at resolutions and sensitivities exceeding those afforded by conventional optical microscopic techniques. Advantageously, such events can be monitored in real time and in an aqueous environment unlike those lyophilised conditions necessary for visualisation of such interactions by electron microscopy.

The range of the types of particle which can be individually seen by the process of the invention is also varied and broad. The use of the optical element herein described, by virtue of its ability to facilitate the generation of detectable optical signals from sub-micron particulates, allows the process of the invention to be applied to the estimation of contaminant levels in process or industrial fluids and liquids which are desired to be contaminant free, the detection of virus particles and other sub-micron biological entities in biological, environmental, biotechnological, foodstuff and clinical samples, such as blood and urine and other body fluids, purification media, pharmaceutical preparations, foodstuffs and the like. Very sub-micron particles designed to act as fluorescent labels, such as those referred to as quantum dots, are equally amenable to detection and analysis. Other particulates in solution or suspended in a fluid phase that may be individually detected, counted and characterised in accordance with the invention include contaminating organic or inorganic particles in otherwise particle free fluids, smoke or other combustion product particles in gases, contaminants in oils, micro-emulsion (oil in water or water in oil) droplets, liposomes and vesicles, micelles, sub-microscopic cells such as mycoplasmas, colloids of natural or industrial origin, or any suspension, colloidal fluid or preparation in which light scattering centres exist and which are too small too be analysed by conventional optical instrumentation. It will, of course, be appreciated that the process of the invention allows any particulate capable of scattering or modifying radiation incident upon it and which can be distinguished from the background by a suitable detector to be individually detected and analysed.

It will be further appreciated that the process of the invention is applicable to the analysis of individual macromolecules and macromolecular constructs which, through labelling with a suitable optical amplifier or fluorescent label capable allowing them to be distinguished from the background if required, would not otherwise be detectable on an individual basis using conventional optically based particle characterising instrumentation. Equally the invention may be applicable in situations wherein the detectable particles are part of a larger supramolecular structure, such as a cell or cellular component, a biofilm, polymeric layer or the like.

The use of the partially metallised optical element illuminated with a suitable optical source as described herein is particularly advantageous in that readily available light sources of modest power such as low cost gas, diode or solid state lasers can be used in conjunction with conventional detection optics and electronic photosensitive devices to detect particles which normally would only be capable of being individually visualised by very much more sophisticated and complex techniques such as electron microscopy.

It should be noted that the invention is not confined to the case where samples are in solution. Where they are however, the solvent need not be water or even liquid but the solution may take the form of any form known to physical chemistry in which particles can be optically differentiated from their surrounding environment for analytical purposes. Furthermore, it should be clear that the process of the invention can be applied to situations in which the particulates to be detected and individually visualised are acted on by other physical forces, such as electrical or acoustic fields, so as to, for instance, induce physical motion or separation from other constituents in the sample.

Besides the embodiments of the method and the apparatus described above the invention can be used in a variety of other configurations and for a variety of other purposes. Thus, besides the incorporation of the invention into a JOOS type flow cytometric configuration it could be incorporated into any other optical detection apparatus in which the interaction of very small particles with an optical field is measured. For instance, the invention could be incorporated into a scanning probe microscope, such as a scanning near-field microscope, as a means of visualising a surface and locating desirable or interesting features on that surface to assist in the efficient high resolution scanning and imaging of the surface by the scanning probe tip.

Similarly, the invention could be used to monitor and analyse the dynamic Brownian motion of the particles thus visualised, information from which can, by suitable analytical techniques such as number fluctuation spectroscopy and fluorescence correlation spectroscopy or point tracking image analysis equipment, be used to derive a range of particle characteristics such as size and size distribution, number, concentration and the nature and dynamics of particle-particle interactions or interactions of the particles with a functionalised layer, if present.

Similarly, the invention could be used to enhance the performance of and derive more information from other analytical techniques such as Surface Plasmon Resonance (SPR) apparatus allowing SPR device surfaces to be simultaneously analysed for particulates in any given sample under analysis.

It should also be noted that small particulates interacting with the optical field present at or close to the surface of the optical element described herein, can be subject to physical motive forces from the light itself, a phenomenon known as photophoresis. This ability to modify the physical motion of particles, for instance effectively trap them in a certain location by the pressure of light alone, could be used to advantage in the analysis and manipulation of particles in accordance with the invention.

Particular benefits which ensue from the invention include the ability to directly and individually visualise sub-microscopic particles such as viruses and other particles in the 5-500 nm diameter range which have not necessarily had to be optically amplified by use of fluorophore or light scattering labels and which would not otherwise be detectable by conventional microscope instrumentation. Analytical resolution is greatly improved by the ability afforded by the invention to characterise and analyse on a particle-by-particle basis a population of particles that may be diverse in size and optical properties and, if desired, to determine the spatial distribution of said particles. Furthermore, the ability to monitor the dynamic behaviour of particles suspended in a liquid by sophisticated analytical techniques such as digital or optical correlation of signals emanating from the particles is valuable in determining other physical properties and characteristics of submicron particles that might not otherwise be obtainable by other techniques. The physical components from which the apparatus can be assembled are not complex or expensive and can be used by non-expert users. The apparatus lends itself to being retrospectively fitted to a range of existing optical analytical instrumentation and instrumentation designs to improve resolution and performance.

The invention will now be described in more detail by way of example with particular reference to the accompanying schematic drawings of which;

EXAMPLES

Figure 1:
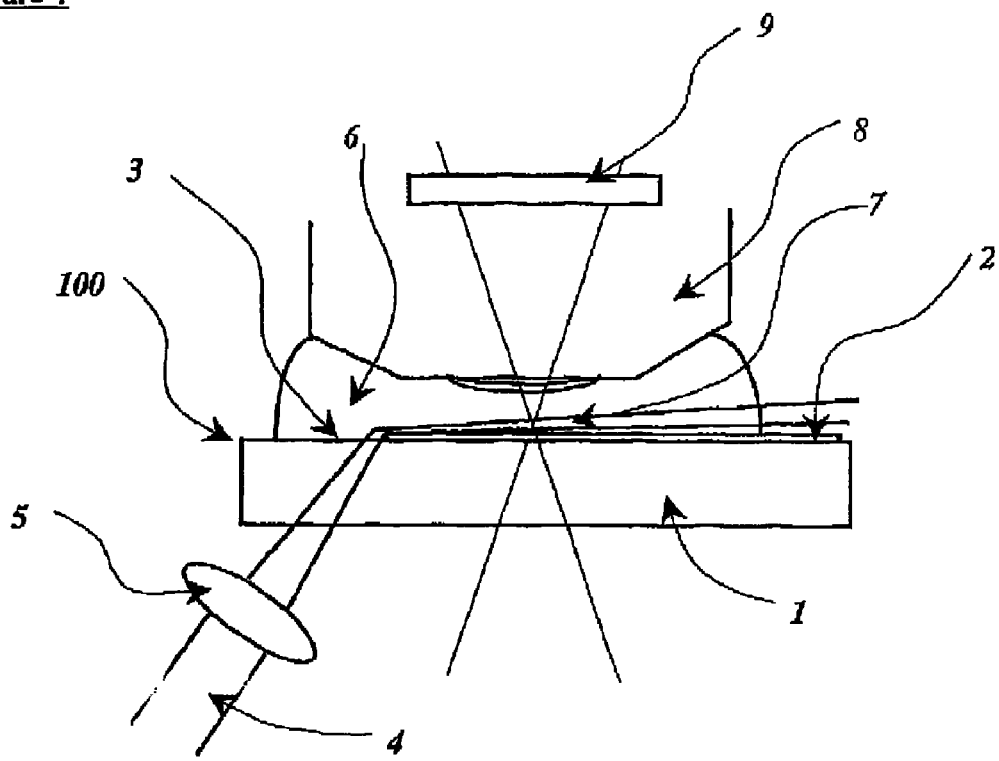
FIG. 1 illustrates apparatus according to the invention for the detection of sub-micron particles such as viruses suspended in an aqueous fluid.

Referring to FIG. 1, apparatus in accordance with the invention comprises an instrument element 100 having an optically transparent substrate 1, typically a glass or silica prism or flat, onto part of which is deposited a thin film of metal 2, typically 30-80 nm depth of e.g. gold, silver, aluminium or chrome deposited by any suitable sputtering, vapour phase, electrochemical or other deposition means. The optical substrate is only partially covered by the metal film 2, a portion 3 of the surface being left uncoated. A light beam of suitable collimation, intensity, polarisation and wavelength or wavelength range 4 is focused by lens 5 to be incident on the optical element such that the beam strikes the surface of the optical element in the region 3 which is not covered by the metal fil 2 but which is adjacent to the metallised region at an angle at which, when a sample of liquid 6 containing a suspension of particles 7 is placed onto the surface of the optical element 100, the beam is caused, by refraction, to propagate through the sample substantially parallel to and a small distance above the metal film. Those particles 7, present within the beam individually act to scatter light which can be detected in the far field by a suitably aligned and focused lens arrangement 8 such as a microscope objective, which could be an immersion lens, and associated lenses to be subsequently observed by eye or analysed using a photosensitive device and suitable signal processing or image analysis instrumentation. Alternatively, the particles could be viewed through a suitable optically transparent planar window in, for instance, a flow cell arrangement or through a microscope cover slip or equivalent.

It will of course be understood that besides the simple observation of light scattered by particles 7, other optical consequences of their being illuminated by the beam 4 when propagating close to the metal film 2 may be observed and analysed. Thus, if the particle population 7 is comprised entirely or partially of particles which are inherently fluorescent or have been specifically labelled through the use of selected fluorescent labels, those particles which fluoresce on coming into close proximity to the region of the metal coated substrate 2 illuminated by beam 4, may be specifically observed through the lens assembly 8 if the image is first filtered by a suitable fluorescence filter assembly 9.

It will be further understood that the use of several different fluorescence filters will allow multiple wavelengths to be separately analysed extending the information that can be obtained about a multiply stained particle suspension under view.

Figure 2:
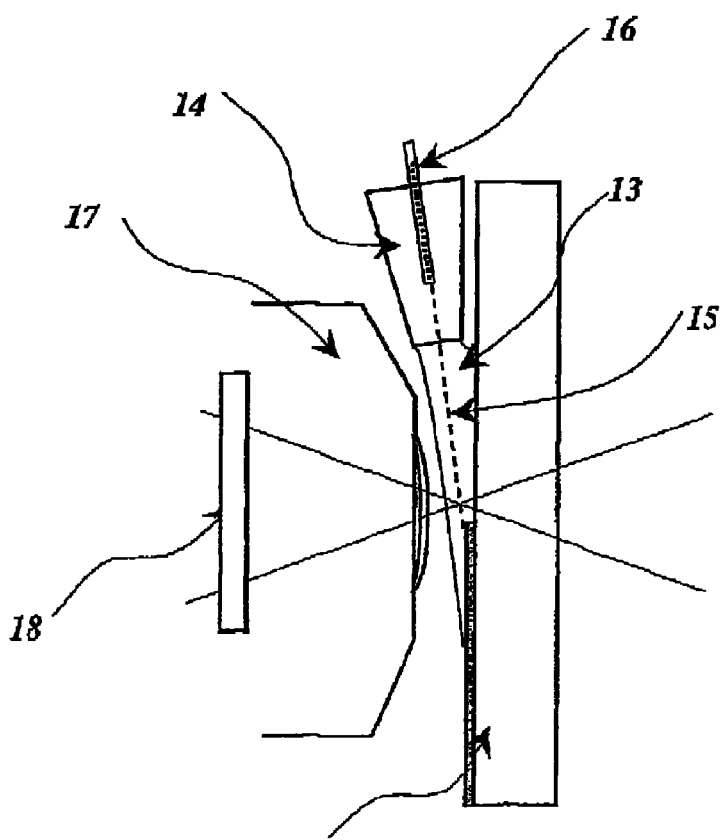
FIG. 2 illustrates one use of the invention for application in a flow cytometric configuration.

In FIG. 2 is shown an alternative apparatus for use in a flow cytometric configuration of the jet-on-an-open-surface type. The optical element shown in FIG. 1 can be mounted in such a way as to allow a stream of particle bearing sample to be flowed across its surface. When a hydrodynamically focused stream of fluid 13 (a "hydrodynamic sheath") emanating from a nozzle 14 and containing a stream of particles 15 introduced into the hydrodynamic sheath fluid by tube 16 is passed through the region at which the optical beam propagates over the metallised region of the optical element 100, particles directed, by fine adjustment of nozzle 14, to flow in close proximity to this region will either scatter light or be induced to fluoresce, the optical radiation of which is detected, through use of lens system 17 containing a fluorescent filter assembly 18, if required, by a suitable photosensitive detector and associated signal processing electronics capable of measuring the optical signal generated by the separate particles at a rate which allows particles to be analysed individually and sequentially at high rates, typically hundreds or thousands per second. The lens assembly 17 can be designed and constructed such that one or more of a variety of angles of scattered light can be selected from the scattered radiation or fluorescence emanating from the particle.

Figure 3:
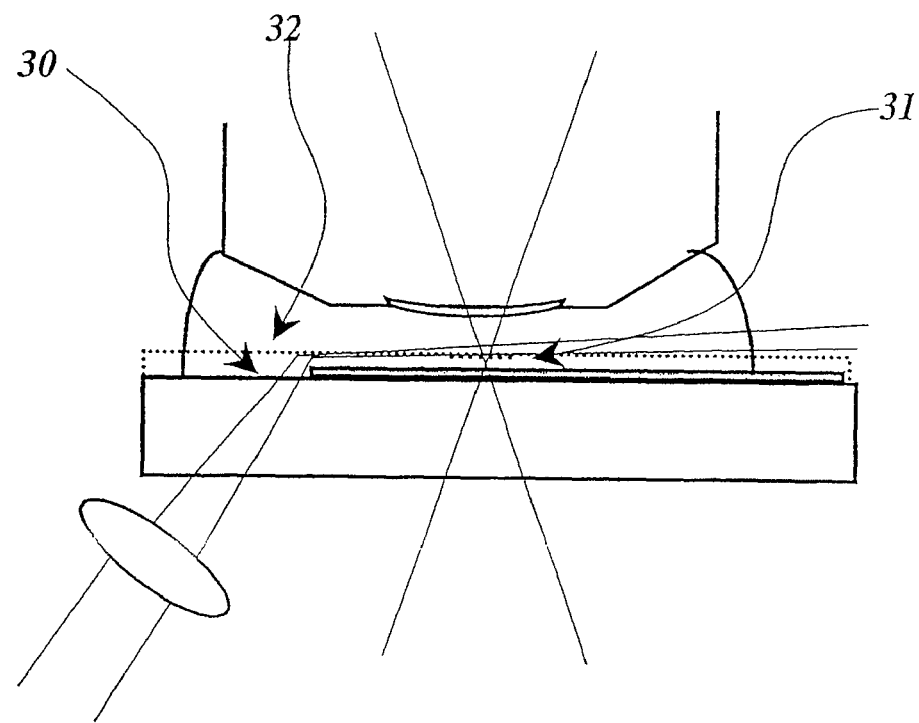
FIG. 3 illustrates the use of the apparatus for studying the interaction of particles with a functional layer deposited on the optical element.

In FIG. 3 is shown an alternative configuration for the detection of interaction of particles with a functional surface comprising an instrument element 100 as shown in FIG. 1 coated with a functional layer 30 which may comprise a polymeric or biological material which substantially replicates the properties exhibited by a natural cell membrane or wall surface and from which the interaction of particles 31 in a liquid sample 32, which may, for instance, be infective virus particles, can be obtained information about the rate, number and behaviour of binding events between the particles and the functional surface. Alternatively, the functional layer may comprise a chemically or biochemically modified layer onto which have been attached chemical or biological molecular moieties such as antibodies or other selective ligand binding structures which exhibit a specific affinity for target molecular or particulate structures 31 the presence and number or other property of which is required to be established in the sample 32.

As in the other embodiments described above, it is of course obvious that besides the simple observation of changes in light scattered by particles 31, other optical consequences of their coming into close proximity to the region of the metal/glass interface illuminated by the optical beam may be observed and analysed. Thus, if the particle population 31 is comprised entirely or partially of particles which are inherently fluorescent or have been specifically labelled through the use of selected fluorescent labels, those particles which fluoresce on coming into close proximity to the region of the metal/glass interface illuminated by the optical beam may be specifically observed through the lens and detection assembly if the image is first filtered by a suitable fluorescence filter. Similarly, rotation of the polarisation of the incident beam by the particles can be measured in this invention.

It will be further understood that the use of several different fluorescence filters will allow multiple wavelengths to be separately analysed extending the information that can be obtained about a multiply stained particle suspension under view.

In the preferred embodiment, the optical element is a silica quartz planar substrate onto which has been deposited by a sputtering method, an approximately 50-80 nm thick layer of chrome. The optical element is illuminated at suitable incident angle by a laser beam of modest power, for example 40 mW and suitable wavelength, for instance 488 nm. A drop of a biological sample such as a sample of clinical or biological origin diluted in phosphate buffered saline containing a population of unlabelled refractile virus particles of clinical or biotechnological significance (such as adenoviruses) is placed on the optical element surface and the light the virus particles scatter as they move under Brownian motion within the optical beam propagating through the sample in close proximity to the metallised region of optical element is observed by eye down a conventional microscope fitted with a ×40 immersion objective. Images of the virus can, of course, be captured on film or on video recording by suitable instrumentation for subsequent viewing and analysis. The presence and number concentration of virus particles in the sample can be determined from the intensity of light they scatter (light scattering in this size region being a strong function, for instance radius, of their size) or from counting the number of points of light of intensity associated with a particle size per unit volume in the sample for any given illumination intensity.

It should be understood that though this invention has been described by way of various examples a variety of modifications are possible without departing from the scope of the appended claims.

The invention claimed is:

1. Apparatus for the optical detection and/or analysis of individual sub-micron particles, the apparatus comprising: a substrate, part of one surface of which is coated with a film comprising an optically opaque metal, and part of which surface is left uncoated, such that the surface has a coated portion and an uncoated portion; means for illuminating said substrate with a focussed beam of radiation from a source, such that a focussed optical beam is caused to be incident on the substrate at a point on the uncoated portion of the surface adjacent to, but not coincident with, the metal film coated portion of the surface, such that the optical beam is caused to propagate above but substantially parallel or at an angle of less than 5° and close to the surface of the metal film; and means for individually detecting, by a lens and detector arrangement situated in the far field at the normal or high angle to the plane of the metal film, the optical radiation individually scattered by, or otherwise caused to emanate from, individual particles in a sample placed on the coated portion of the substrate surface through their interaction with the optical beam.

2. Apparatus according to claim 1, wherein the source is a laser.

3. Apparatus according to claim 1, wherein the substrate is part of a larger assembly designed and constructed for purposes other than particle detection.

4. Apparatus according to claim 1, wherein the lens and detector arrangement comprises a conventional microscope.

5. Apparatus according to claim 1, in combination with a flow cytometer instrument.

6. Apparatus according to claim 1, wherein the substrate comprises or is formed from a wholly or partially optically transparent material.

7. Apparatus according to claim 1, wherein the focussed optical beam is incident upon one surface of the substrate, is refracted during passage through the substrate, and emerges at the opposite surface at a slight angle adjacent or close to the metal film coated portion of said surface.

8. A microscope or flow cytometer comprising apparatus in accordance with claim 1.

9. Apparatus according to claim 1, wherein the focused optical beam is caused to be incident on the substrate at a point on the uncoated portion of the surface within 5 mm of the metal film coated portion of the surface.

* * * * *